(12) United States Patent
Grisoni et al.

(10) Patent No.: US 6,267,719 B1
(45) Date of Patent: Jul. 31, 2001

(54) MAGNETIC SHEETS

(75) Inventors: Bernard Grisoni, Arlington; Laura Crane, Williston, both of TN (US)

(73) Assignee: Schering-Plough HealthCare Products, Inc., Memphis, TN (US)

( * ) Notice: Subject to any disclaimer, the term of this patent is extended or adjusted under 35 U.S.C. 154(b) by 0 days.

(21) Appl. No.: 09/387,944

(22) Filed: Sep. 1, 1999

(51) Int. Cl.[7] .............................. A61N 1/00; A61B 17/52
(52) U.S. Cl. ............................................................ 600/15
(58) Field of Search ............................................ 600/9–15

(56) References Cited

U.S. PATENT DOCUMENTS

| | | | |
|---|---|---|---|
| 4,033,054 | * 7/1977 | Fukuoka | 600/15 |
| 4,549,532 | * 10/1985 | Bearmann | 600/15 |
| 5,158,526 | * 10/1992 | Bricot | 600/9 |
| 5,233,768 | 8/1993 | Humphreys . | |
| 5,304,111 | 4/1994 | Mitsuno et al. . | |
| 5,538,495 | * 7/1996 | Ardizzone | 600/9 |
| 5,871,438 | 2/1999 | Ardizzone . | |
| 5,965,282 | 10/1999 | Baermann . | |

FOREIGN PATENT DOCUMENTS

| | | | |
|---|---|---|---|
| 1450093 | * 12/1966 | (FR) | 600/15 |
| 830172 | * 12/1984 | (NL) | 600/15 |

* cited by examiner

Primary Examiner—Samuel G. Gilbert
(74) Attorney, Agent, or Firm—Robert J. Lipka

(57) ABSTRACT

A magnetic sheet comprising permanent magnetic particles arranged in a pattern to form alternating elongated zones of first and second opposite polarities, each zone being defined by spaced apart parallel zigzag boundary lines formed by a plurality of equal length, substantially linear segments which meet at point contacts to form sharp turns, with angles formed at the sharp turns and defined by connected segments being 90/, each zone of the first polarity being bounded by only two zones of the second polarity positioned on opposite sides thereof, and each zone of the second polarity being bounded by only two zones of the first polarity positioned on opposite sides thereof. The magnetic sheet of the invention has many applications, including a removable insole for insertion into footwear.

6 Claims, 8 Drawing Sheets

MAGNETIC SHEETS

BACKGROUND OF THE INVENTION

The present invention relates generally to a magnetic sheet having two-dimensional alternating poles. Such magnetic sheets may be used in a wide range of applications, including shoe insoles for shoes that have magnetic particles embedded therein.

Insoles have generally been formed by a pad of cushioning material, such as sponge rubber, that has a general shape conforming to the interior of a shoe. Wearers who desire additional shoe comfort or who suffer from foot trouble, for example, plantar heel pain and/or arch pain, insert the cushioned insole into the shoe to provide added cushioning and support.

It is also known to provide insoles with magnetic particles therein. The magnetic particles are arranged in areas of alternating polarity. The reason for providing the magnetic particles is to increase blood flow and thereby accelerate healing of injured body parts. The basic theory is that charged particles in the blood stream, such as calcium ions, sodium chloride ions, electrolytes and the like, which are used for various purposes such as repairing bone and tissue, etc., are forced by the changing magnetic polarities through which the blood vessel passes, to move from one side of the blood vessel to the other side of the blood vessel as they travel along the blood vessel. This creates heat and helps to accelerate blood flow by bringing more blood to the blood vessel.

U.S. Pat. No. 4,489,711 to Latzke discloses the use of alternating stripes of unidirectional north and south magnetic poles. However, when the blood vessel extends in the same direction as the magnetic stripes, there is no alternating magnetic field, and no therapeutic effect. See also U.S. Pat. No. 5,233,768 to Humphreys for a similar disclosure.

U.S. Pat. No. 4,549,532 to Baermann discloses alternating magnetic areas formed as concentric rings or radial sectors. However, for blood vessels, which are positioned near the periphery of the concentric ring arrangement, the effect is less effective, since the blood vessel will traverse an area of only one polarity. The reverse is true for the radial sectors, since a blood vessel passing through the center will traverse only an area of only one polarity.

U.S. Pat. Nos. 5,277,692; 5,514,072; 5,538,495; and 5,871,438, all to Ardizzone, attempt to overcome the problems with the above patents. Specifically, Ardizzone provides a spiral arrangement of magnetic areas of alternating polarity, with the areas reducing in size toward the outside and inside of the spiral. This arrangement is provided to take into account all random positions of the blood vessels, to ensure that the blood vessels, regardless of orientation, always traverse alternating polarity areas. The problem arises, however, in the manufacture of this pattern. This is because of the complexity of the pattern, and the fact that it provides little tolerance for offsets during manufacturing. Thus, if there is any offset in the magnetic areas from the desired pattern, the position of entire pattern is thrown off.

The Ardizzone patents also provide an alternative checkerboard pattern of alternating polarity areas. Each area of one polarity is surrounded by either three or four areas of opposite polarity. However, with this arrangement, areas of opposite polarity contact each other at corner points to provide alternating zones of opposite polarity. This also provides little tolerance for variations in manufacture, and makes manufacture thereof extremely difficult.

U.S. Pat. No. 5,304,111 to Mitsuno et al discloses alternating sinusoidal areas of opposite polarity. However, when dealing with such sinusoidal patterns, it may be difficult to maintain an exact pitch of each boundary line relative to an adjacent boundary line, and an exact spacing between the boundary lines. Even with the exact arrangement of Mitsuno et al, the boundary lines come close to each other, and thereby come close to approximating the checkerboard pattern of the Ardizzone patents. Mitsuno et al also discloses a polka dot pattern. However, Mitsuno et al admits that a blood vessel can be aligned to run along only a zone of south polarity. In such case, even if a blood vessel overlies adjacent zones of alternating north and south polarity, the magnetic pull on opposite sides will be equal and cancel out, thereby having no affect on the charged particles in the blood vessel.

Other patents of interest are U.S. Pat. Nos. 4,033,054 (Fukuoka), 4,079,526 (Fukuoka), 4,109,661 (Fukuoka), 4,223,458 (Kihara), 4,270,966 (Kihara), 4,727,661 (Kuhn), 4,843,738 (Masuda), 5,553,398 (Schnewlin-Maier), 5,685,094 (Lin) and 5,738,624 (Zablotsky et al).

The entire disclosures of all of the aforementioned U.S. Patents are incorporated herein by references.

SUMMARY OF THE INVENTION

Accordingly, it is an object of the present invention to provide a magnetic sheet that overcomes the problems with the aforementioned art.

It is another object of the present invention to provide a magnetic sheet which may be applied to the body in which the magnetic particles are arranged in areas of alternating polarity to increase blood flow and accelerate healing of injured body parts.

It is still another object of the present invention to provide a magnetic sheet in which blood vessels will traverse areas of alternating magnetic polarity, substantially regardless of the orientation of the blood vessels.

It is yet another object of the present invention to provide such a magnetic sheet that has a relatively simple repeating pattern.

It is still another object of the present invention to provide a magnetic sheet that provides a desired alternating polarity effect, while providing sufficient tolerance during the manufacturing process, without substantially affecting the predetermined pattern.

It is yet another object of the present invention to provide a magnetic sheet having elongated zigzag zones of opposite polarity which alternate with each other, with the zigzag zones being defined by parallel, spaced apart zigzag boundary lines.

It is a further object of the present invention to provide a magnetic sheet in which discrete areas of one polarity are separated by a sea of an opposite polarity, and in which the discrete areas are arranged so as to prevent a blood vessel from overlying only the sea of opposite polarity without also overlying a discrete area.

The magnetic sheets of the present invention have many applications and may be incorporated, for example, in any device applied proximate to the body. Such devices include, for example, an insole, mattress, seat cover, and pads, wraps or bands for head, waist, ankle, knee, shoulder or back.

The magnetic sheet may preferably be incorporated into a removable insole for insertion into footwear, which may include a flexible layer of cushioning material having permanent magnetic particles embedded therein.

The permanent magnetic particles are arranged in a pattern to form alternating elongated zones of first and second opposite polarities, each zone being defined by spaced apart zigzag boundary lines. Each zone of the first polarity is bounded by only two zones of the second polarity positioned on opposite sides thereof, and each zone of the second polarity is bounded by only two zones of the first polarity positioned on opposite sides thereof.

The zigzag boundary lines are parallel to each other and are spaced apart by a first distance for the zones of the first polarity and a second distance for the zones of the second polarity. Preferably, the first and second distances are equal to each other.

The zigzag boundary lines are formed by a plurality of substantially linear segments, which meet at point contacts to form sharp turns. In one embodiment, the segments are all of equal lengths, and in another embodiment, there are at least two the segments of different lengths for each the zigzag boundary line. The angles formed at the sharp turns and defined by connected segments are between the approximate range of 10/ and 170/. In one embodiment, the angles are each approximately 90/, and in another embodiment, at least two of the angles for each zigzag boundary line are different.

In accordance with another aspect of the present invention, the permanent magnetic particles are arranged in a pattern to form first discrete island areas of a first polarity completely separated from each other by a second area of a second opposite polarity in completely surrounding relation to the first discrete areas. The first discrete island areas are arranged such that a blood vessel overlying the pattern will always overlie both the first discrete island areas and the second area, regardless of an orientation of the blood vessel.

Preferably, each of the first discrete island areas has a polygonal configuration. The first discrete island areas can be arranged in a regular repeating pattern or in a random pattern.

In accordance with another aspect of the present invention, the permanent magnetic particles are arranged in a pattern to form first discrete island areas of a first polarity completely separated from each other by a second area of a second opposite polarity in completely surrounding relation to the first discrete areas. The first discrete island areas are arranged in an offset manner such that a blood vessel overlying substantially only the second area will be bounded on opposite sides thereof by the first discrete island areas in an asymmetric arrangement in a lengthwise direction of the blood vessel.

Preferably, each of the first discrete island areas has a polygonal configuration, and are arranged in a regular repeating pattern.

In accordance with another aspect of the present invention, the permanent magnetic particles are arranged in a pattern to form alternating elongated zones of first and second opposite polarities, each zone being defined by spaced apart elongated boundary lines. Each zone of the first polarity is bounded by only two zones of the second polarity positioned on opposite sides thereof, and each zone of the second polarity is bounded by only two zones of the first polarity positioned on opposite sides thereof. Further, each elongated zone has extension zones of the same polarity connected therewith and extending at an angle to a direction of extension of the respective elongated zone toward an adjacent elongated zone.

Preferably, the elongated boundary lines having a generally sinusoidal waveform shape, and the extension zones have a generally L-shaped configuration and extend substantially perpendicular to the elongated zones.

The above and other features of the invention will become readily apparent from the following detailed description thereof, which is to be read in connection with the accompanying drawings.

DETAILED DESCRIPTION

Figure 1:
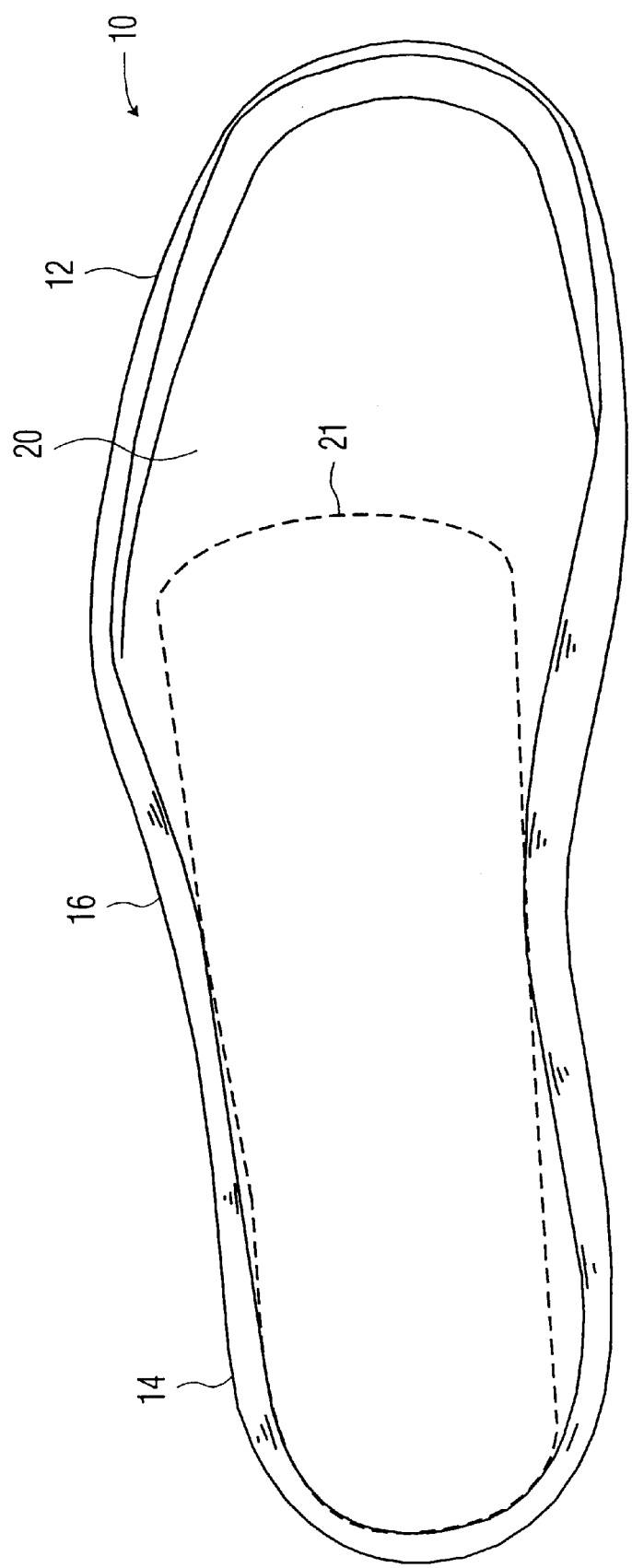
FIG. 1 is a top plan view of a magnetic sheet according to the present invention.
Figure 2:
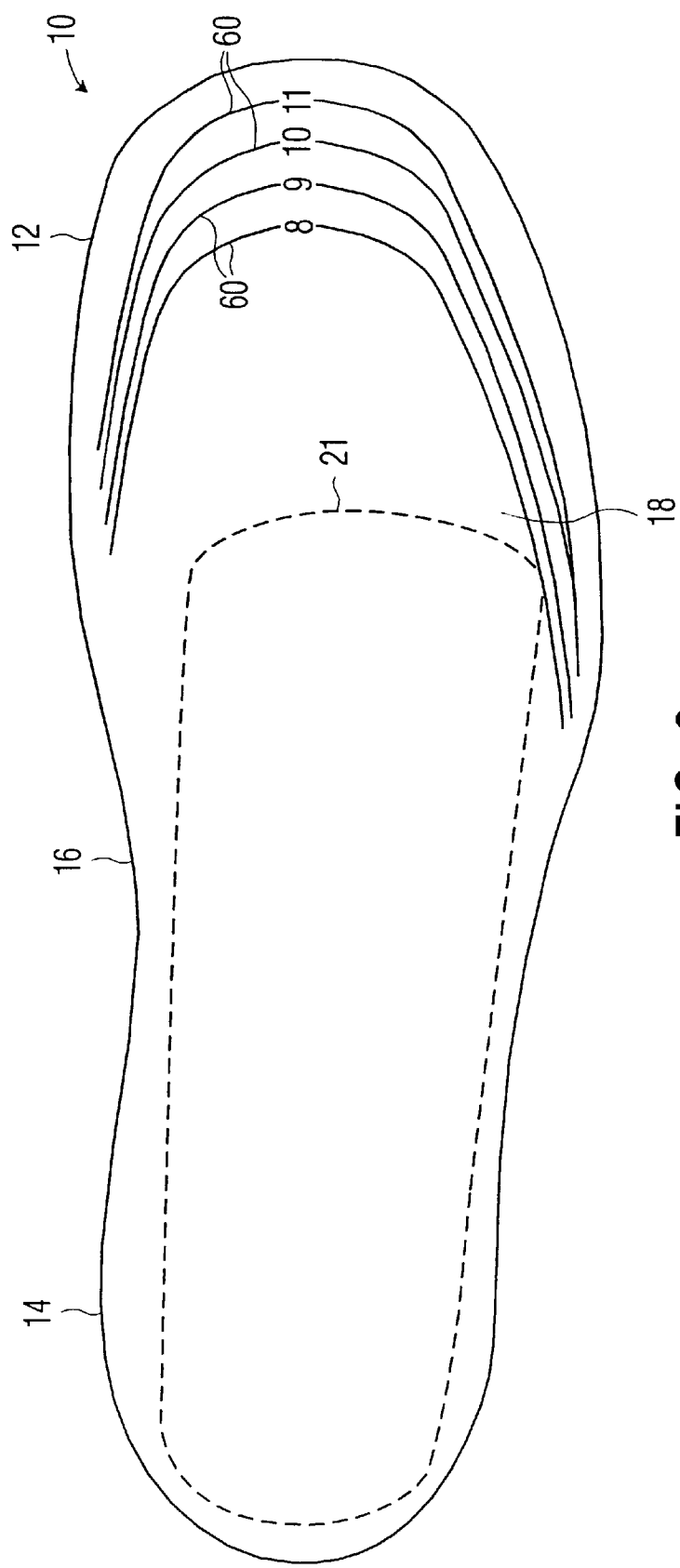
FIG. 2 is a bottom plan view of the magnetic sheet.

Referring to the drawings in detail, and initially to FIGS. 1 and 2 thereof, an insole 10 according to the present invention is adapted to be placed in an article of footwear, as is well known. Accordingly, insole 10 has the shape of a human left foot and has a companion (not shown) for the right foot which is formed in a mirror image.

Insole 10 therefore includes a curved toe portion 12, a heel portion 14, and a medial arch portion 16 which connects toe portion 12 and heel portion 14 together. Heel portion 14 preferably has a greater thickness than toe portion 12 since the greater impact during walking and running occurs at the heel. For example, heel portion 14 can have a thickness of approximately 7–8 cm and toe portion 12 can have a thickness of approximately 2–3 cm. In addition, opposite sides of medial arch portion 16, and opposite sides and the rear end of heel portion 14, gently slope downwardly and inwardly toward the lower surface of insole 10.

Insole 10 is formed of a lower layer 18 made of a foam, gel or the like, and a top cover 20 secured to the upper surface of lower layer 18 by any suitable means, such as adhesive, RF welding, etc. Both layers 18 and 20 are preferably formed of a fluid impermeable material.

In accordance with one aspect of the present invention, magnetic particles, such as ferrite particles, are embedded in the device in a specific pattern. Specifically, the ferrite particles are placed with the powder used to mold the remainder of lower layer 18, and then the mixture is placed in a mold under high temperature and pressure to form the desired shape, as is conventional. The desired magnetic pattern can be formed using a magnetizer with an opposite magnetic pattern to the desired magnetic pattern, and which magnetizes the ferrite particles into the desired pattern. The ferrite particles can be positioned in devices such as insole 10, or alternatively, can be positioned in only a portion of insole 10, for example, as shown by dashed line 21 in FIGS. 1 and 2.

In accordance with the present invention, elongated contiguous areas or zones 22 and 24 of permanent magnetic particles having opposite polarities, that is, north (N) polarity for zones 22 and south (S) polarity for zones 24, are arranged in an alternating or interleaved manner. Zones 22 and 24 are parallel to each other, so that blood vessels crossing over zones 22 and 24 overlie zones 22 and 24 in an alternating manner. Specifically, in accordance with the present invention, zones 22 and 24 are arranged in a zigzag manner, that is, with outer boundaries defined by zigzag boundary lines 26 that are parallel and spaced apart from each other. It is important that zigzag boundary lines 26 change their directions at corner points 28, thereby changing direction at sharp angles or sharp turns. Zones 22 and 24 can extend at any angle relative to the lengthwise direction of insoles 10, for example, zones 22 and 24 can extend along the lengthwise direction of insole 10 at 0/, at a 45/ angle to the lengthwise direction, in the widthwise direction of insole 10 at a 90/ angle, or any other suitable angle.

It will be appreciated that various advantages derive from such zigzag zones 22 and 24 defined by zigzag boundary lines 26. Specifically, unlike the Ardizzone patents, there is no contact between adjacent zones 22 and 24 at only a point contact. This enables the magnetized pattern to be formed easily in a manufacturing operation, without worrying about close tolerances. In other words, even if there is some offset or deviation from the exact pattern, the same general pattern will result and will not be adversely affected thereby. Unlike the Ardizzone patents, each zone of one polarity is bordered by only two zones of opposite polarity, for example, each north polarity zone 22 is bordered by only two south polarity zones 24. This provides that zones 22 and 24 meet only along zigzag boundary lines 26, and not only at a point contact as in the Ardizzone patents.

At the same time, however, because of zigzag boundary lines 26, that is, boundary lines formed by lines that constantly change direction at sharp corner points 28, there is a greater probability that a blood vessel which travels in the same direction as zones 22 and 24 will overlap at least two zones of opposite polarity, in order to achieve the desired effect.

This same advantage applies over the arrangement of U.S. Pat. No. 4,489,711 to Latzke in which the elongated zones are straight, that is, have linear, spaced apart boundary edges. In the arrangement of Latzke, if a blood vessel runs along one zone, there will be no change in polarity. This is overcome to a large extent by zigzag boundary lines 26 of the present invention, so that there is a greater chance of a blood vessel overlying zones 22 and 24 of opposite polarities.

Further, by forming zigzag boundary lines 26 from linear, or substantially linear, segments 30 that meet at sharp corner points 28, it becomes easier to form the patterns and easier to manufacture with greater tolerance, than can be achieved with the sinusoidal wave pattern of U.S. Pat. No. 5,304,111 to Mitsuno et al. In addition, the width of each zone 22 and 24, as measured in a direction transverse to the lengthwise direction thereof, is substantially constant, varying only by a small amount, which is not the case with the Mitsuno et al waveform, in which the boundary lines come close to each other, and thereby come close to approximating the checkerboard pattern of the Ardizzone patents.

Figure 3:
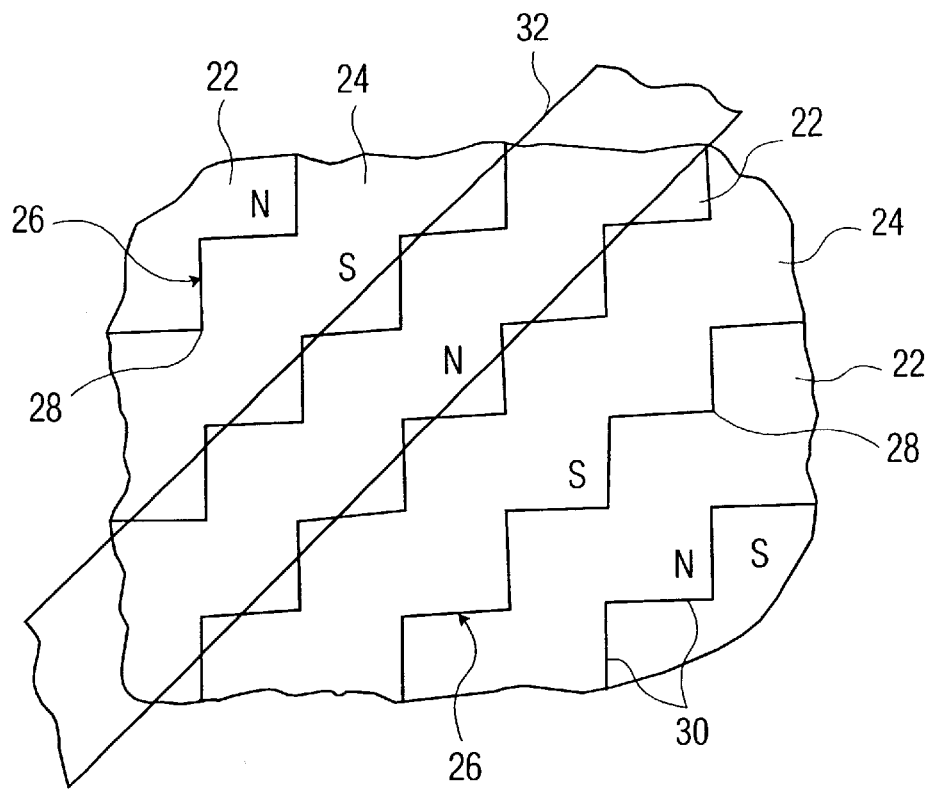
FIG. 3 is a top plan view of a magnetic pattern within the magnetic sheet according to a first embodiment of the present invention.

Still further, even if a blood vessel 32 runs in the lengthwise direction of a zone 22, as shown in FIG. 3, the adjacent zones 24 on opposite sides of the zone 22 will not be symmetrical relative to zone 22, as measured in the widthwise direction of zone 22, because of the zigzag pattern, so that there will still be some alternating north and south polarities. Therefore, unlike the polka dot pattern of Mitsuno et al, the magnetic pull on opposite sides will be not be equal and will not cancel out, thereby having an affect on the charged particles in the blood vessel.

Figure 4:
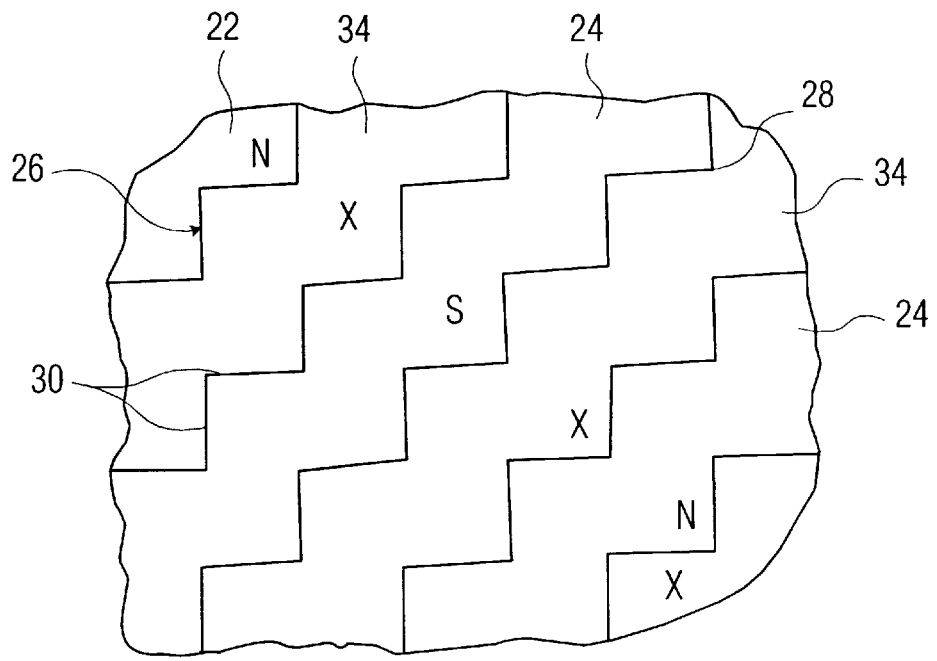
FIG. 4 is a top plan view of a magnetic pattern within the magnetic sheet according to a second embodiment of the present invention.

It is also possible to provide a non-magnetic zone 34 of no polarity (X) between zones 22 and 24 of opposite polarity, to achieve substantially the same effect, as shown in FIG. 4.

Although zigzag boundary lines 26 of FIGS. 3 and 4 have been shown to change angles at 90/ to each other at corner points 28 in a step-like manner, the present invention is not limited thereby. Thus, the angle can be 130/ (FIG. 5), 40/ (FIG. 6) or any other suitable angle, but preferably within the range of approximately 10/ to 170/.

Figure 5:
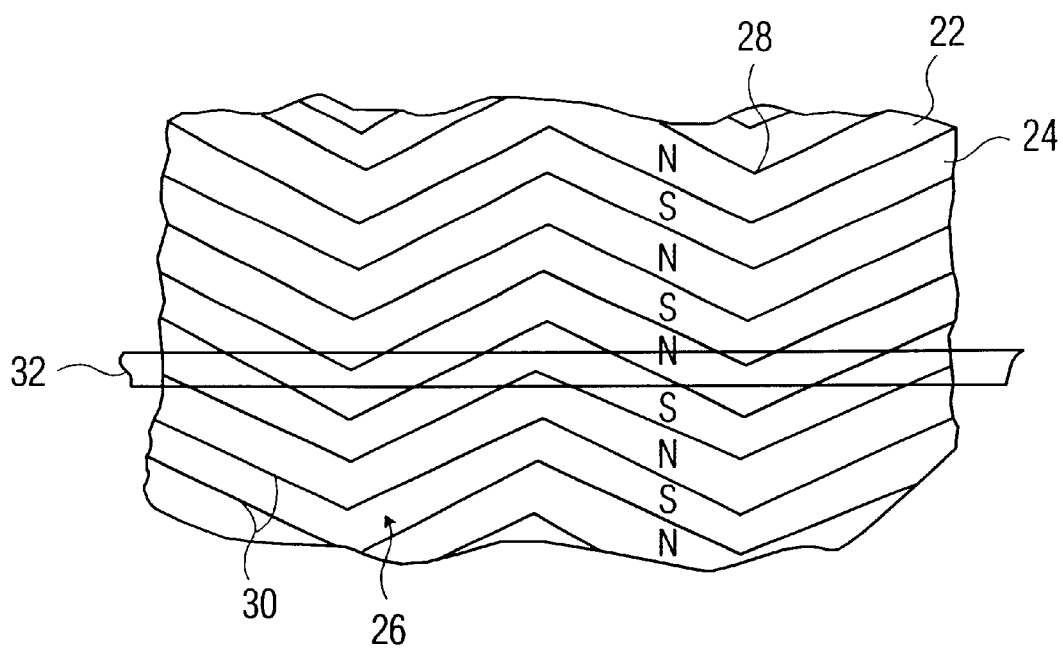
FIG. 5 is a top plan view of a magnetic pattern within the magnetic sheet according to a third embodiment of the present invention.
Figure 6:
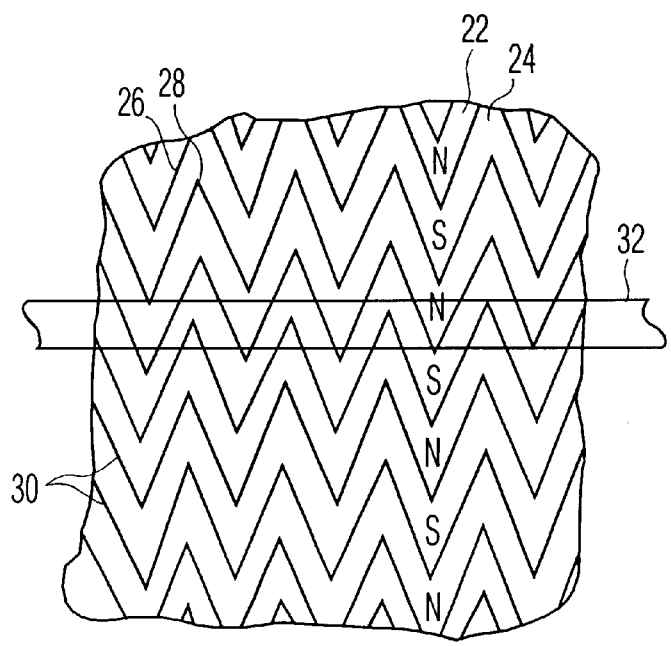
FIG. 6 is a top plan view of a magnetic pattern within the magnetic sheet according to a fourth embodiment of the present invention.

Still further, by providing sharp angles between linear segments 30 of zigzag boundary lines 26, the spacing between boundary lines 26 can be easily changed from the larger spacing of FIGS. 3 and 4 to the narrower spacing of FIGS. 5 and 6, without changing the uniform or constant width of zones 22 and 24, unlike the waveform boundary lines of Mitsuno et al, which would eventually meet at point contacts, thereby effectively forming the checkerboard pattern of the Ardizzone patents.

As another advantage, by reducing the spacing between zigzag boundary lines 26, the probability of a blood vessel overlying only one zone 22 or 24 is eliminated, as clearly evident by blood vessel 32 shown in FIGS. 5 and 6.

Figure 7:
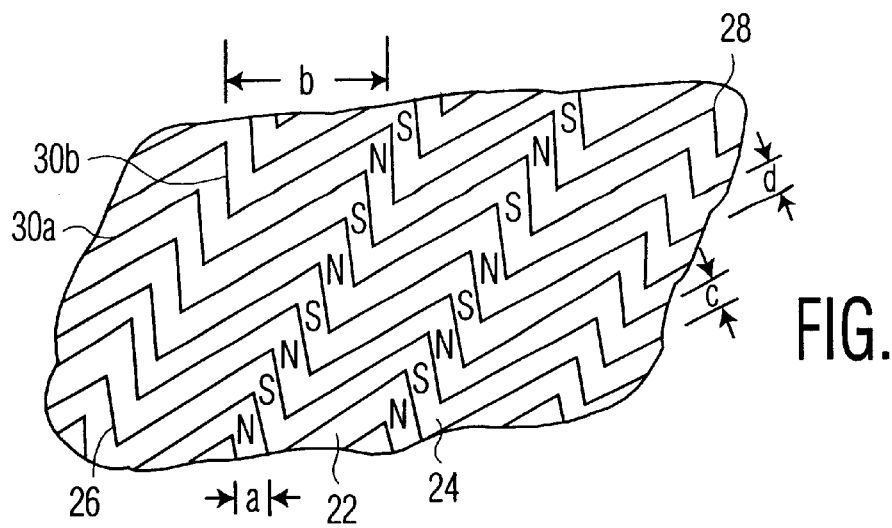
FIG. 7 is a top plan view of a magnetic pattern within the magnetic sheet according to a fifth embodiment of the present invention.

Further, although zigzag boundary lines 26 have been shown to be formed of equal length segments 30 in an isosceles arrangement in FIGS. 3–6, the present invention is not limited thereto, and can be formed of segments 30a and 30b of unequal length, as shown by the saw-tooth arrangement in FIG. 7. In such case, the angles therein can also be formed in the range of approximately 10/ to 170/. FIG. 7 shows this angle to be about 60/. This further reduces the possibility that a blood vessel will overlie only one zone 22 or 24. As an example, and with reference to FIG. 7, the length "a" can be in the range of 1 to 25 mm, and preferably, 5 to 16 mm. The length "b" can be in the range of 1 to 100 mm, and preferably, 5 to 16 mm. The length "c" can be in the range of 1 to 25 mm, and preferably, 5 to 16 mm. The length "d" can be in the range of 1 to 100 mm, and preferably, 5 to 16 mm. However, the present invention is not limited to these lengths.

It will therefore be appreciated that, in addition to segments 30a and 30b having different lengths, the width of zones 22 and 24 can be different, that is, the length "c", which corresponds to the width of zones 22, can have a different width than the length "d" which corresponds to the width of zones 24.

Figure 8:
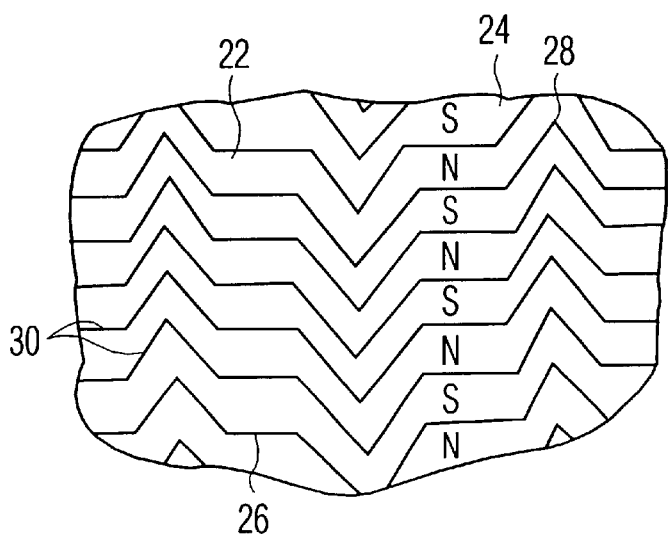
FIG. 8 is a top plan view of a magnetic pattern within the magnetic sheet according to a sixth embodiment of the present invention.
Figure 9:
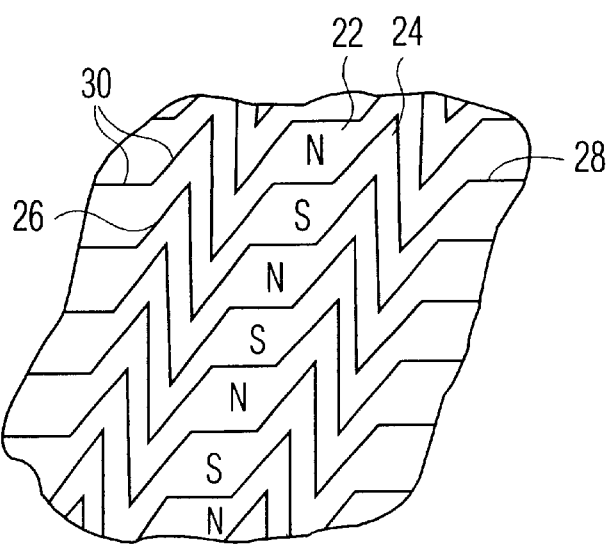
FIG. 9 is a top plan view of a magnetic pattern within the magnetic sheet according to a seventh embodiment of the present invention.

Although zigzag boundary lines 26 of FIGS. 3–7 are shown to have equal angles throughout lines 26, that is, 90/ in FIGS. 3–6 and 60/ in FIG. 7, the angles along zigzag boundary lines 26 can vary along the length thereof, as shown in FIGS. 8 and 9, as long as the angles of adjacent boundary lines 26 vary in the same manner, in order to achieve a substantially constant width of each zone 22 and 24. For example, in FIG. 8, starting from the left end of any boundary line 26, the angle between segments 30 varies as approximately 120/, 60/, 120/, 120/, 120/, 60/, 120/, 120/, 60/ and 120/. In FIG. 9, starting from the left end of any boundary line 26, the angle between segments 30 varies as approximately 130/, 40/, 40/, 130/, 130/, 40/, 40/ and 130/.

Therefore, the embodiments of FIGS. 3–9 share the common features of providing parallel zigzag zones 22 and 24 defined by parallel zigzag boundary lines 26 formed by substantially linear segments 30 which meet at point contacts 28 to form sharp turns or angles, and with a substantially constant spacing between boundary lines 26.

Referring now to FIGS. 10–16, a magnetic pattern can be formed of discrete areas or magnetic islands 40 of one polarity in a magnetic sea 42 of an opposite polarity, which surrounds islands 40. Islands 40 can take any shape, such as triangular (FIG. 10), square (FIGS. 11 and 12), diamond (FIG. 13), hexagonal (FIG. 14) or any other suitable shape, formed in a regular, repeating pattern.

Figure 11:
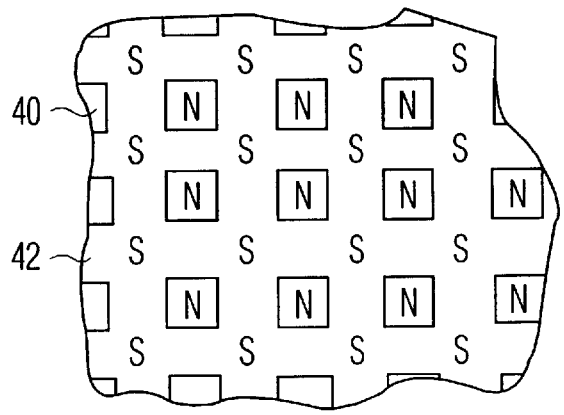
FIG. 11 is a top plan view of a magnetic pattern within the magnetic sheet according to a ninth embodiment of the present invention.

The arrangement of FIG. 11 suffers from similar deficiencies as the polka dot pattern of Mitsuno et al in permitting a blood vessel to travel along only a zone of one polarity. For example, in the polka dot pattern of Mitsuno et al, when a blood vessel travels along the sea or background of south polarity, it is bounded on opposite sides by islands of north polarity in a symmetric arrangement, so that the north polarity islands would have no affect in that they would cancel out on opposite sides.

Figure 12:
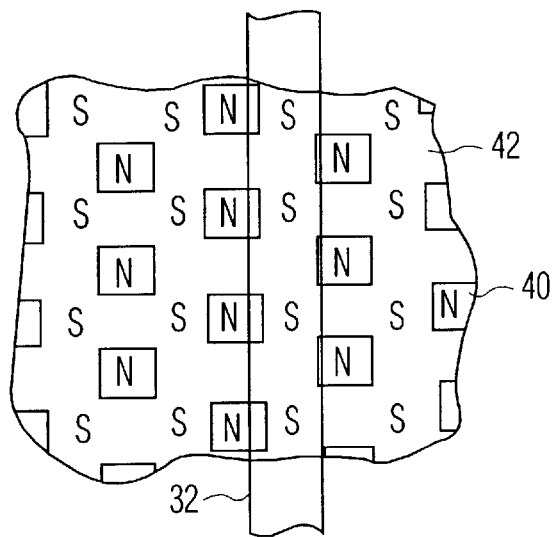
FIG. 12 is a top plan view of a magnetic pattern within the magnetic sheet according to a tenth embodiment of the present invention.

However, in the arrangement of FIG. 12, if a blood vessel 32 travels in the vertical direction of the figure, the north polarity islands 40 are offset so as to present an asymmetrical arrangement, and thereby affect the charged particles in the blood, to move the charged particles from one side to the other. The same affect would occur with the arrangement of FIG. 14 if a blood vessel moves along a diagonal of the figure so as to be substantially in overlying relation to the sea of south polarity.

Figure 13:
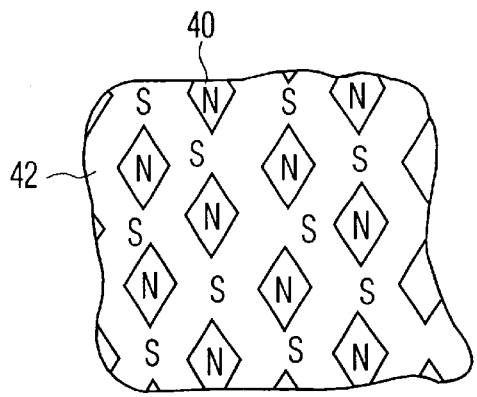
FIG. 13 is a top plan view of a magnetic pattern within the magnetic sheet according to an eleventh embodiment of the present invention.
Figure 14:
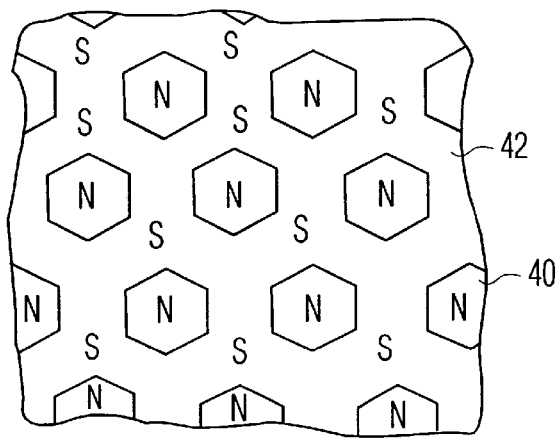
FIG. 14 is a top plan view of a magnetic pattern within the magnetic sheet according to a twelfth embodiment of the present invention.

In FIG. 13, the diamond shaped islands 40 are preferably offset from each other so that travel only along the south polarity sea 42 cannot be achieved, that is, such travel, regardless of the orientation of the blood vessel, will always overlie at least some islands 40 of north polarity.

Figure 10:
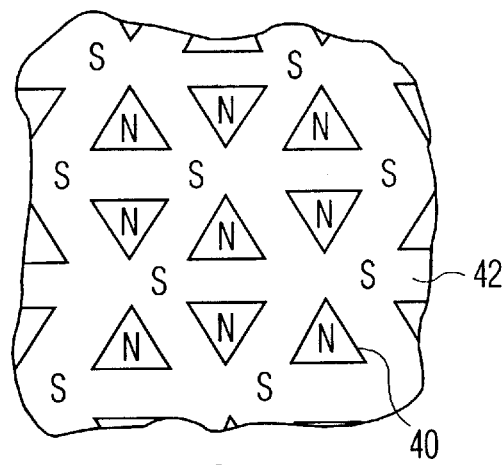
FIG. 10 is a top plan view of a magnetic pattern within the magnetic sheet according to an eighth embodiment of the present invention.

Because of the inverted arrangement of triangular islands 40 of north polarity in FIG. 10, this same effect is achieved.

Figure 15:
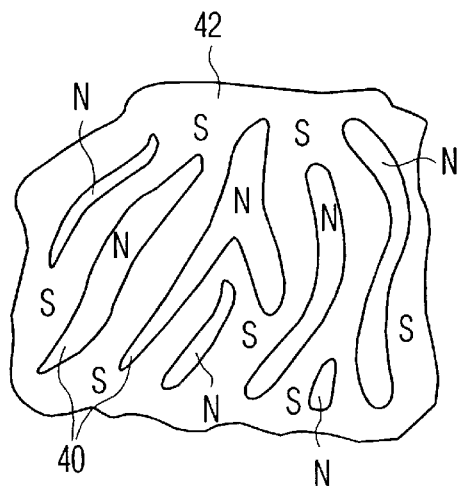
FIG. 15 is a top plan view of a magnetic pattern within the magnetic sheet according to a thirteenth embodiment of the present invention.
Figure 16:
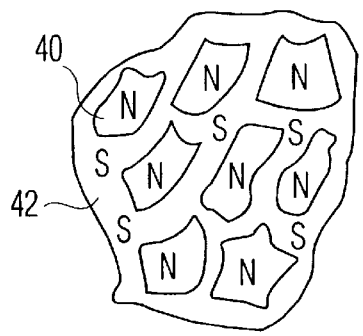
FIG. 16 is a top plan view of a magnetic pattern within the magnetic sheet according to a fourteenth embodiment of the present invention.

FIG. 15 shows islands 40 of north polarity in a zebra stripe arrangement in a sea 42 of south polarity. FIG. 16 shows islands 40 of north polarity in a giraffe marking arrangement in a sea 42 of south polarity. In such case, FIGS. 15 and 16 effectively have a random arrangement of islands 40 of north polarity in a sea 42 of south polarity, so that it becomes effectively impossible for a blood vessel to overlie only one polarity, regardless of the orientation of the blood vessel.

Thus, the patterns of FIGS. 10–16 share the common features of islands 40 of a north polarity in a sea 42 of an opposite south polarity, preferably in a manner such that a blood vessel cannot overlie only the sea 42 of south polarity, and even if it can, as in the embodiment of FIG. 12, there will be an arrangement of asymmetric islands 40 on opposite sides thereof.

Figure 17:
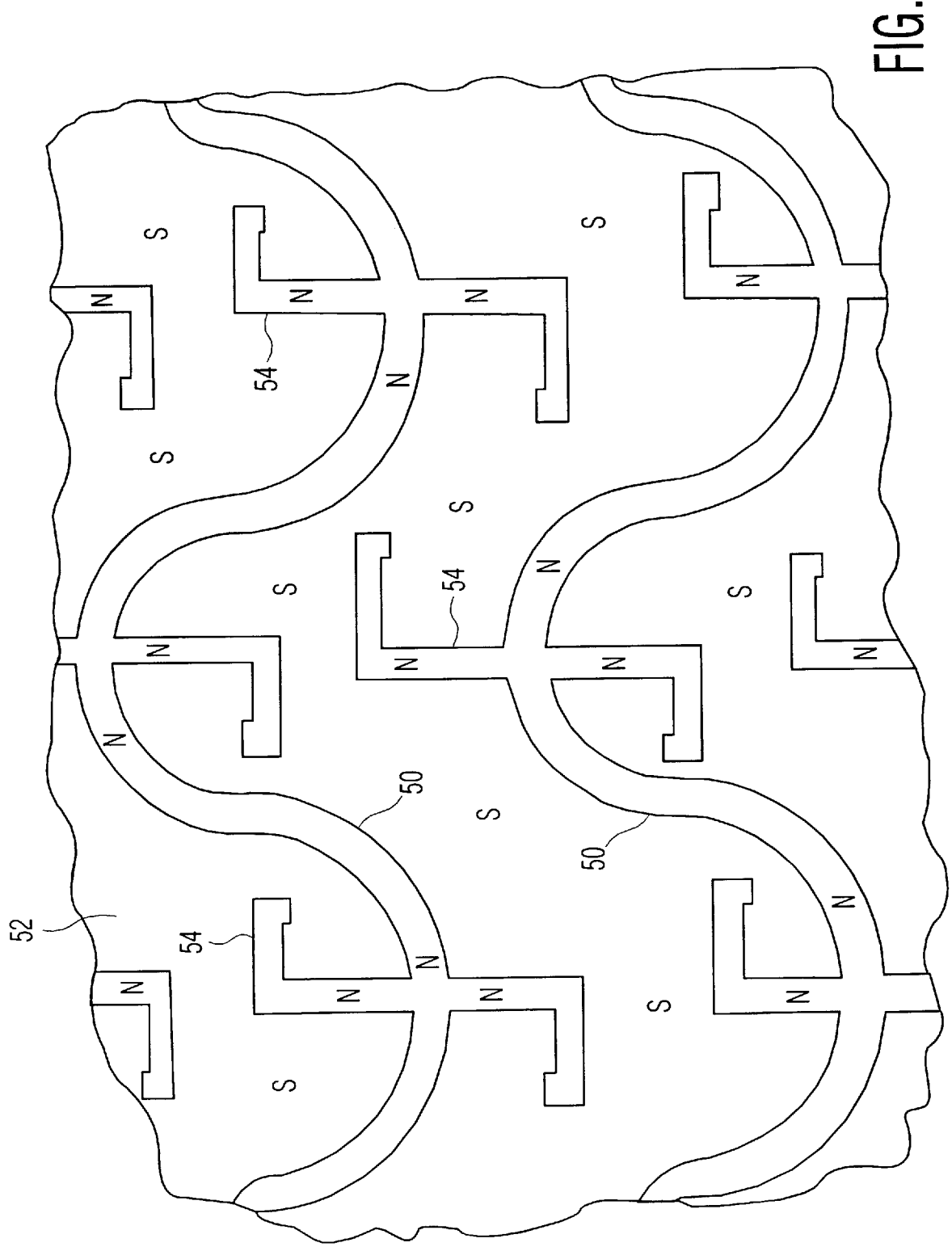
FIG. 17 is a top plan view of a magnetic pattern within the magnetic sheet according to a fifteenth embodiment of the present invention.

FIG. 17 shows a complicated repeating pattern according to another embodiment of the present invention. Specifically, with this arrangement, there are parallel, spaced apart, sinusoidal wave zones 50 of north polarity in a sea 52 of south polarity in much the same manner as Mitsuno et al. However, in addition, parallel, spaced apart L-shaped or J-shaped zones of north polarity are connected with and extend away from zones 50 of north polarity. L-shaped (or J-shaped) zones 54 of north polarity are connected to adjacent sinusoidal wave zones 50 face in an opposite direction. As a result of this arrangement, a blood vessel must overlie alternating zones of north and south polarity, and cannot overlie only sea 52 of south polarity.

Referring back to FIGS. 1 and 2, top layer 20 can be made from any suitable material such as fabric, leather, leather board, expanded vinyl foam, flocked vinyl film, coagulated polyurethane, latex foam on scrim, supported polyurethane foam, laminated polyurethane film or in-mold coatings such as polyurethane, styrene- butadiene-rubber, acrylonitrile-butadiene, acrylonitrile terpolymers and copolymers, vinyls, or other acrylics, as integral top covers. Desirable characteristics of top cover 20 include good durability, stability and visual appearance. Also desired is that the material of top cover 20 have good flexibility, as indicated by a low modulus, in order to be easily moldable. The bonding surface of top cover 20 should provide an appropriate texture in order to achieve a suitable mechanical bond to lower layer 12. Preferably, top cover 20 is a fabric, such as a brushed knit laminate top cloth (brushed knit fabric/urethane film/non-woven scrim cloth laminate) or a urethane knit laminate top cloth.

Further, insole 10 would be typically sized to correspond to different shoe sizes and provided in sized pairs. Alternatively, insole 10 may be trimmed to the requirements of the user. In this regard, arcuate pattern trim lines 60 may be formed on the lower surface of toe portion 12 of insole 10, and which are representative of various sizes of the human foot. For example, insole 10 may be provided for a men's shoe size of 12, continuous pattern trim lines 60 being representative of smaller size insoles for men's shoe sizes of 8, 9, 10 and 11. If the user requires a size other than the original large size 12, the wearer merely trims the insole with a scissors or cutting instrument, using pattern trim lines 60, to achieve the proper size. The pattern trim lines may be imprinted by conventional printing techniques, silkscreening and the like. As an alternative, pattern trim lines 60 may be formed as shallow grooves, or be perforated, so that a smaller size insole may be separated by tearing along the appropriate trim lines, which tearing operation is facilitated by the inclusion of perforations.

Although the present invention has been disclosed relative to a full length insole, it will be appreciated that an insole according to the present invention can be made other than a full length insole, such as a three quarter length insole, that is, where the length extends from the heel to the first metatarsals of the foot, or any other suitable arrangement.

Although the present invention uses the term insole, it will be appreciated that the use of other equivalent or similar terms such as innersole or insert are considered to be synonymous and interchangeable, and thereby covered by the present claimed invention.

Having described specific preferred embodiments of the invention with reference to the accompanying drawings, it will be appreciated that the present invention is not limited to those precise embodiments and that various changes and modifications can be effected therein by one of ordinary skill in the art without departing from the scope or spirit of the invention as defined by the appended claims.

REFERENCE DESIGNATOR 10 insole
12 toe portion
14 heel portion
16 medial arch portion
18 lower layer
20 top cover
22 elongated zones
24 elongated zones
26 zigzag boundary lines
28 corner points
30 linear segments
32 blood vessel
34 non-magnetic zone
40 magnetic islands of one polarity
42 sea of opposite polarity
50 sinusoidal wave zones of one polarity
52 sea of opposite polarity
54 L-shaped zones
60 pattern trim lines

What is claimed is:

1. A magnetic sheet comprising permanent magnetic particles arranged in a pattern to form alternating elongated zones of first and second opposite polarities, each zone being defined by spaced apart zigzag boundary lines, each zone of the first polarity being bounded by only two zones of the second polarity positioned on opposite sides thereof, and each zone of the second polarity being bound by only two zones of the first polarity positioned on opposite sides thereof, wherein said zigzag boundary lines are formed by a plurality of substantially linear segments which meet at point contacts to form sharp turns.

2. A magnetic sheet according to claim 1, wherein said segments are all of equal lengths.

3. The magnetic sheet of claim 1 wherein said magnetic sheet is an insole.

4. A magnetic sheet according to claim 1, wherein said zigzag boundary lines are parallel to each other.

5. A magnetic sheet according to claim 4, wherein said zigzag boundary lines are spaced apart by a first distance for said zones of said first polarity and a second distance for said zones of said second polarity.

6. A magnetic sheet according to claim 5, wherein said first and second distances are equal to each other.

* * * * *